United States Patent
Giri et al.

(10) Patent No.: US 12,246,318 B2
(45) Date of Patent: Mar. 11, 2025

(54) DEVICES AND METHODS FOR SENSING AND SORTING PARTICLES

(71) Applicant: TDK Corporation, Tokyo (JP)

(72) Inventors: Manish Giri, San Jose, CA (US);
Rakesh Sethi, San Jose, CA (US);
Vadim Piskun, San Jose, CA (US)

(73) Assignee: TDK CORPORATION, Tokyo (JP)

( * ) Notice: Subject to any disclaimer, the term of this patent is extended or adjusted under 35 U.S.C. 154(b) by 554 days.

(21) Appl. No.: 17/589,593

(22) Filed: Jan. 31, 2022

(65) Prior Publication Data
US 2023/0241611 A1 Aug. 3, 2023

(51) Int. Cl.
*B01L 3/00* (2006.01)
*C12Q 3/00* (2006.01)
(Continued)

(52) U.S. Cl.
CPC .......... *B01L 3/502761* (2013.01); *C12Q 3/00* (2013.01); *B01L 2200/027* (2013.01); *B01L 2200/0652* (2013.01); *B01L 2300/0645* (2013.01); *B01L 2300/0663* (2013.01); *B01L 2300/0864* (2013.01); *B01L 2300/12* (2013.01); *G01N 2015/0019* (2013.01); *G01N 2015/1006* (2013.01); *G01N 2015/1027* (2024.01); *G01N 15/1031* (2013.01)

(58) Field of Classification Search
CPC ....... B01L 2200/027; B01L 2200/0652; B01L 2300/0645; B01L 2300/0663; B01L 2300/0864; B01L 2300/12; B01L 2400/0415; B01L 2400/0439; B01L 3/502715; B01L 3/50273; B01L 3/502761; C12Q 3/00; G01N 15/1023; G01N 15/1031; G01N 2015/0019; G01N 2015/1006; G01N 2015/1027; G01N 2015/1028
See application file for complete search history.

(56) References Cited

U.S. PATENT DOCUMENTS 4,756,427 A 7/1988 Gohde et al.
5,837,200 A * 11/1998 Diessel ................... B03C 1/035
 209/567

(Continued)

OTHER PUBLICATIONS

International Search Report and Written Opinion dated Jun. 23, 2023, issued in corresponding International Patent Application No. PCT/US2023/011677.

*Primary Examiner* — Jennifer Wecker
*Assistant Examiner* — Britney N. Washington
(74) *Attorney, Agent, or Firm* — Morgan, Lewis & Bockius LLP

(57) ABSTRACT

A microfluidic device and a method for sensing and sorting of cells or particles in a microfluidic channel are disclosed. The microfluidic device may include a substrate with a microfluidic channel having an inlet, the microfluidic channel being coupled with two or more output channels; one or more sensors located adjacent to a first region of the microfluidic channel for sensing respective particles flown through the microfluidic channel; and a first piezoelectric actuator located adjacent to a second region of the microfluidic channel downstream from the first region for deflecting the respective particles flowing through the microfluidic channel to respective output channels of the two or more output channels based on signals from the one or more sensors.

20 Claims, 5 Drawing Sheets

(51) Int. Cl.
    *G01N 15/00*     (2024.01)
    *G01N 15/10*     (2024.01)
    *G01N 15/1031*     (2024.01)

(56) References Cited

U.S. PATENT DOCUMENTS

| | | | |
|---|---|---|---|
| 6,838,056 B2 * | 1/2005 | Foster | B01L 3/502761 |
| | | | 436/63 |
| 6,951,632 B2 | 10/2005 | Unger et al. | |
| 9,821,310 B2 * | 11/2017 | Guldiken | G01N 33/5005 |
| 10,207,269 B2 | 2/2019 | Ismagilov et al. | |
| 10,578,633 B2 | 3/2020 | West et al. | |
| 2004/0161772 A1 * | 8/2004 | Bohm | G01N 15/1456 |
| | | | 435/6.16 |
| 2006/0121555 A1 * | 6/2006 | Lean | B03C 5/028 |
| | | | 435/297.2 |
| 2008/0011058 A1 | 1/2008 | Lal et al. | |
| 2012/0162664 A1 * | 6/2012 | Bakke | G01J 3/26 |
| | | | 359/872 |
| 2015/0024373 A1 * | 1/2015 | Xia | F04B 43/043 |
| | | | 435/308.1 |
| 2015/0112490 A1 * | 4/2015 | Calderon | B01L 3/502761 |
| | | | 700/282 |
| 2015/0268029 A1 * | 9/2015 | Rowat | G01N 29/036 |
| | | | 435/287.1 |
| 2016/0003729 A1 | 1/2016 | Lo et al. | |
| 2016/0158758 A1 | 6/2016 | Johnson et al. | |
| 2016/0193613 A1 | 7/2016 | Walti et al. | |
| 2016/0202172 A1 | 7/2016 | Guck et al. | |
| 2017/0248512 A1 * | 8/2017 | Di Carlo | G01N 15/1429 |

\* cited by examiner

DEVICES AND METHODS FOR SENSING AND SORTING PARTICLES

TECHNICAL FIELD

This application relates generally to sensing and sorting of cells or particles, and more particularly to sensing and sorting of cells or particles based on phenotype analysis.

BACKGROUND

Conventional techniques for single cell analysis rely on external flow systems (i.e., not integrated within the microfluidic device). However, such an external flow control system typically is slow to activate and does not provide precise control of the flow dynamics in the microfluidic device for reliable cell capture, localization, and analysis. Further, cells are "charged" prior to deflection in an electric field, which can harm the cells, and cells are sensed optically using fluorescent tagging, which means that there is a pre-treatment step to functionalize the cells. Moreover, such cell sorting is only binary in nature, i.e., the sorting only provides indication whether a cell is of interest or not, but fails to categorize and sort cells of different types in a single device.

SUMMARY

The devices and methods described herein address challenges associated with conventional devices and methods for sensing and sorting particles or cells in microfluidic devices or systems.

In accordance with some embodiments, a microfluidic device includes a substrate with a microfluidic channel having an inlet, the microfluidic channel being coupled with two or more output channels; one or more sensors located adjacent to a first region of the microfluidic channel for sensing respective particles flown through the microfluidic channel; and a first piezoelectric actuator located adjacent to a second region of the microfluidic channel downstream from the first region for deflecting the respective particles flowing through the microfluidic channel to respective output channels of the two or more output channels based on signals from the one or more sensors.

In accordance with some embodiments, a method includes providing a plurality of particles through a microfluidic channel having an inlet, the microfluidic channel being coupled with two or more output channels; sensing respective particles flowing through the microfluidic channel with one or more sensors located adjacent to a first region of the microfluidic channel; and directing the respective particles flown through the microfluidic channel to respective output channels of the two or more output channels based on signals from the one or more sensors using a first piezoelectric actuator located adjacent to a second region of the microfluidic channel downstream from the first region.

Thus, the disclosed devices and methods relate to cell sensing and sorting techniques which are implemented within or as part of a microfluidic device, and the cell sorting is based on information (e.g., signals) regarding the cells being analyzed as captured or sensed by the sensor(s). This sensing information is used to accordingly actuate a piezoelectric actuator such that oscillations generated by the piezoelectric actuator create displacement as well as acoustic waves to deflect or direct the sensed cells toward a desired output channel for collection or ejection. The disclosed devices and methods may replace, or complement, conventional devices and methods.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

DESCRIPTION OF EMBODIMENTS

Reference will be made to embodiments, examples of which are illustrated in the accompanying drawings. In the following description, numerous specific details are set forth in order to provide a thorough understanding of the various described embodiments. However, it will be apparent to one of ordinary skill in the art that the various described embodiments may be practiced without these particular details. In other instances, methods, procedures, components, circuits, and networks that are well-known to those of ordinary skill in the art are not described in detail so as not to unnecessarily obscure aspects of the embodiments.

It will be understood that, although the terms first, second, etc. may be used herein to describe various elements, these elements should not be limited by these terms. These terms are only used to distinguish one element from another. For example, a first cantilever could be termed a second cantilever, and, similarly, a second cantilever could be termed a first cantilever, without departing from the scope of the various described embodiments. The first cantilever and the second cantilever are both cantilevers, but they are not the same cantilever.

The terminology used in the description of the embodiments herein is for the purpose of describing particular embodiments only and is not intended to be limiting of the scope of claims. As used in the description and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Figure 1:
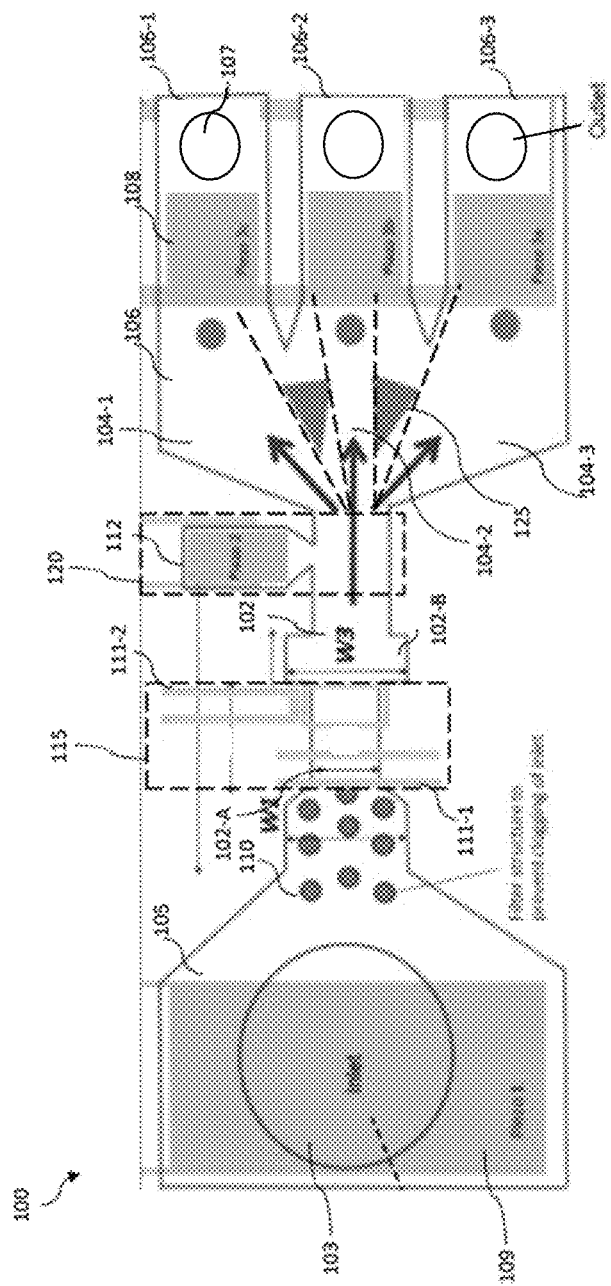
FIG. 1 shows a microfluidic device for sensing and sorting cells in a microfluidic channel in accordance with some embodiments.

FIG. 1 shows a microfluidic device 100 in accordance with some embodiments. The device 100 includes a fluid channel 102 (e.g., a microfluidic channel) formed on a substrate. In some embodiments, the fluid channel 102 may be formed by coupling a first substrate with an indentation, recess, or notch with a second substrate so that the fluid channel 102 is defined between the first substrate and the second substrate. In some embodiments, the first substrate is made of glass and the second substrate is made of silicon-on-insulator (SOI) semiconductor structure.

The fluid channel 102 has an inlet 103 and is coupled with a plurality of output channels, e.g., output channels 104-1, 104-2, and 104-3. In some embodiments, a width W1 (e.g., a representative portion, such as 102-A, which may be the narrowest portion) of the fluid channel 102 may be configured based on the size of the particle to be analyzed. For example, for cellular measurements, the width W1 at the portion 102-A of the fluid channel 102 is configured in accordance with the size of the cell such that only a single cell is detected at a time. In some embodiments, the width W1 of the fluid channel 102 is in the range of 10 microns to 1000 microns (e.g., 50 microns).

In some embodiments, the fluid channel 102 includes one or more portions that have a width different from the width W1. For example, as shown in FIG. 1, the fluid channel 102 may include a portion (or expansion region) 102-B having a (protruding) shape such that the width W3 of the portion 102-B is greater than the width W1. Similarly, the fluid channel 102 may include one or more portions with widths narrower than the width W1. In some embodiments, the wider the fluid channel 102 is, the slower is the velocity of the particles flowing in the corresponding portion of the fluid channel 102 (e.g., when the fluid channel 102 has a uniform height). As such, for example, the wider portion 102-B (having width W3) is used to reduce the velocity of the particles (e.g., immobilize the particles), which allows for more time for analyzing the particles.

The device 100 also includes an input region 105 for receiving at the inlet 103 a sample fluid with particles (e.g., cells) as an input to the device 100 and providing the sample fluid from the inlet 103 to the fluid channel 102. The device 100 further includes an output region 106 for collecting at least a portion of the sample fluid from the fluid channel 102 and ejecting or delivering the sample fluid portion via, e.g., a nozzle for further processing or analysis.

The output region 106 includes the plurality of output channels 104-1, 104-2, and 104-3 and a plurality of output sub-regions (e.g., sub-regions 106-1 through 106-3). In some embodiments, each of the output sub-regions 106-1 through 106-3 includes an outlet port 107 and a piezoelectric actuator 108 (e.g., a piezo micro-electro-mechanical system (MEMS) actuator). In some embodiments, each of the piezoelectric actuators 108 is located adjacent to the respective output channel (e.g., one of the output channels 104-1, 104-2, and 104-3) for ejecting one or more particles. In some embodiments, one or more of the piezoelectric actuators 108 include a layer of piezoelectric material coupled to silicon on insulator. Each of the piezoelectric actuators 108 may include two or more piezoelectric actuators elements (e.g., each element being a MEMS actuator). The piezoelectric element may have a length equal to 1 mm and a width equal to 0.5 mm. In some embodiments, the device 100 includes actuation circuitry (e.g., actuation circuitry 310 described with respect to FIG. 3) electrically coupled to each of the piezoelectric actuators 108 (e.g., via electrodes). In some embodiments, upon application of an electrical signal from the actuation circuitry, the piezoelectric actuators 108 generate oscillations that create displacement as well as acoustic waves, which controls localized inertial movement of the particles in the fluid channel 102 in the three-dimensional x, y and z planes with sub-micron level control.

In some embodiments, each of different portions (e.g., each portion corresponding to a particular cell or a type of cell) of the sample fluid from the fluid channel 102 is deflected toward a corresponding output sub-region of the output region 106. As such, each of the different portions of the sample fluid is collected at and ejected from the corresponding output sub-region. The deflection of the different portions of the sample fluid may be achieved, for example, by the oscillations and displacement caused by the activation of one or more piezoelectric actuators implemented in or operationally associated with the device 100 (as discussed in detail below).

In some embodiments, the input region 105 includes a piezoelectric actuator 109 located adjacent to the inlet 103 for inducing mixing and disassociation of the sample fluid. In some embodiments, the piezoelectric actuator 109 includes two or more piezoelectric actuators elements (e.g., each element being a MEMS actuator). In some embodiments, piezoelectric actuator 109 is electrically coupled to the actuation circuitry (e.g., actuation circuitry 310 described with respect to FIG. 3) via electrodes. Upon application of an electrical signal from the actuation circuitry, the piezoelectric actuator 109 generates oscillations that create displacement as well as acoustic waves which causes mixing of the sample fluid and controls localized inertial movement of the particles to induce a laminar flow in the fluid channel 102 toward the output region 106 or the output channels 104-1, 104-2, and 104-3.

In some embodiments, the device 100 includes a plurality of pillars 110 (e.g., three-dimensional filter pillars), which cell clogging around a region of the fluid channel 102 where the cells are entering a relatively narrow portion 102-A.

Figure 2:
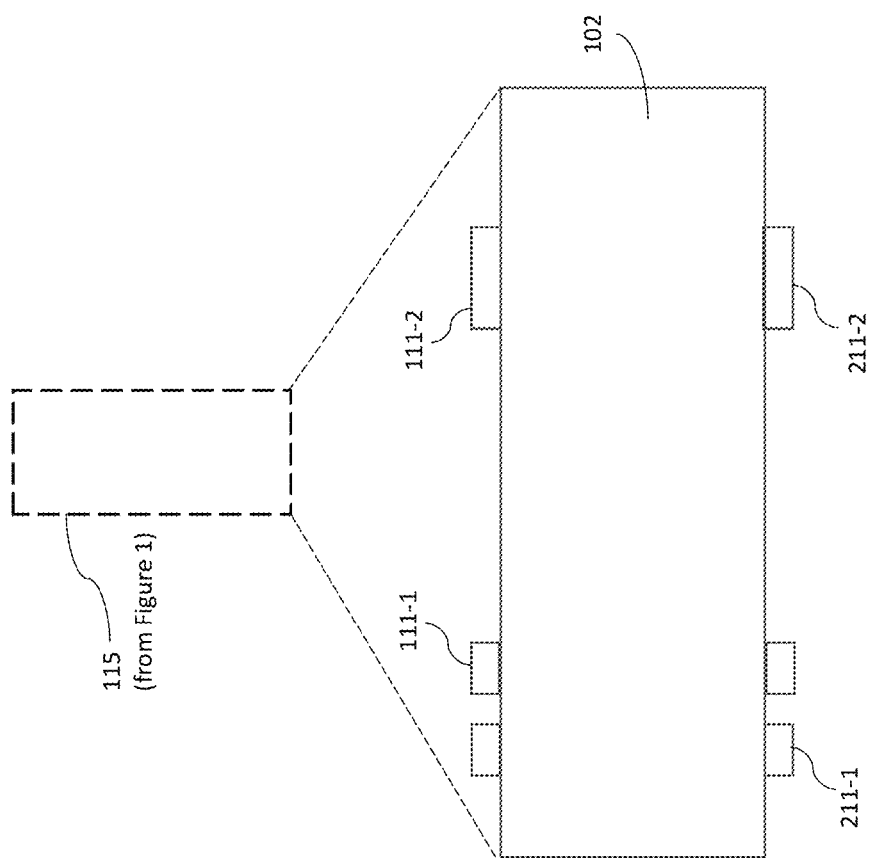
FIG. 2 is a cross-sectional view of the first region of the microfluidic device shown in FIG. 1 in accordance with some embodiments.

In some embodiments, the device 100 includes one or more pairs of electrodes 111 (e.g., electrodes 111-1 and 111-2) and one or more sensors 211 (e.g., sensors 211-1 and 211-2, as shown in and described with respect to FIG. 2) located adjacent to a first region 115 (e.g., a sensing region) of the fluid channel 102. The one or more sensors 211 are used for sensing particles flown through the fluid channel 102. For example, sensing the respective particles includes sensing the respective particles based on their electrical properties (e.g., cell, an encapsulated cell, a particle or a molecule may have electrical properties substantially different from those of the surrounding medium).

In some embodiments, the one or more pairs of electrodes 111 may be used for charging at least a subset of particles flowing through the fluid channel 102 so that the particles can be manipulated with an electrical field. For example, in some operations, some of the particles flowing through the fluid channel 102 may remain non-charged. In some embodiments, an electrical power (e.g., a voltage or current) provided to the one or more pairs of electrodes 111 is modulated to charge only a subset, less than all, of the particles flowing through the fluid channel 102 (e.g., an electrical power provided to the one or more pairs of electrodes 111 is alternatingly switched on and off). In some other operations, all of the particles flowing through the fluid channel 102 are charged. The particles may be charged using electromagnetic radiations of various frequencies from a range of frequencies provided by the electrodes 111. In some embodiments, the distance between a pair of the electrodes 111 (e.g., electrodes 111-1) is configured such that only a single cell is manipulated with an electrical field at a time. In some embodiments, the device 100 includes driver circuitry (e.g., driver circuitry 320 described with respect to FIG. 3) electrically coupled to the one or more pairs of electrodes 111. In some embodiments, the driver circuitry is configured to produce electrical signals in an appropriate frequency domain (e.g., in the megahertz and gigahertz frequency domains). In some embodiments, the frequency of the electrical signals provided to the one or more pairs of electrodes 111 depends on a type or types of the particles to be analyzed using the device 100. In some embodiments, the frequency of the electrical signals provided to the electrodes 111-1 is in the megahertz domain and to the electrodes 111-2 is in the gigahertz domain.

In some embodiments, the one or more pairs of electrodes 111 provide electrical fields for inducing movement of charged particles (e.g., particles charged by the one or more pairs of electrodes 111) or non-charged particles. For example, the electrical fields provided by the one or more pairs of electrodes 111 may induce direct movement of the particles by providing a potential difference. Additionally or alternatively, the electrical fields provided by the one or more pairs of electrodes 111 may induce electrohydrodynamic flow of the fluid (e.g., when the fluid includes dielectric media).

In some embodiments, a separation distance between a pair of electrodes 111-1 as well as a distance between the electrodes 111-1 and the electrodes 111-2 are configured based on a type or types of the particles to be analyzed using the device 100.

Referring to FIG. 2, which is a cross-sectional view of the first region 115 of the fluid channel 102 of the device 100 in accordance with some embodiments. FIG. 2 shows the electrodes 111-1 and 111-2 on one side (e.g., top side) of the fluid channel 102 and the respective sensors 211-1 and 211-2 on another side (e.g., bottom side) of the fluid channel 102. As shown in FIG. 2, in some embodiments, each of the sensors 211-1 and 211-2 is positioned at a location corresponding to a location of the corresponding one of the electrodes 111-1 and 111-2. For example, electrodes 111-1 and 111-2 may be located above the fluid channel 102 and the sensors 211-1 and 211-2 may be located under the fluid channel 102, or vice versa, with their lateral locations corresponding to each other. Each of the sensors 211-1 and 211-2 detects electromagnetic radiations having interacted with a particle (e.g., a cell) for determining an electrical property (e.g., impedance values) of the particle. Such electrical properties of the particle may be used to create phenotype of the particle, which is used to categorize the particle and generate an electrical voltage and pulse to actuate a piezoelectric actuator (e.g., a piezoelectric actuator 112). For example, based on the phenotype of the particle, a deflecting piezo actuation waveform having a certain voltage and pulse width may be generated and provided to the piezoelectric actuator. In some embodiments, the piezoelectric actuator operates under at least two deflection modalities. For example, in one mode, the piezoelectric actuator, when actuated, deflects the particle such that the particle is pushed away from its original position in the fluid channel. In another mode, the piezoelectric actuator, when actuated, deflects the particle such that the particle is pulled closer relative to its original position in the fluid channel.

In some embodiments, the one or more sensors 211-1 and 211-2 include electrodes capable of measuring electrical impedance below 1 GHz. In some embodiments, the one or more sensors 211-1 and 211-2 include electrodes capable of measuring electrical impedance at least at 1 MHz. In some embodiments, the device 100 includes readout circuitry (e.g., readout circuitry 330 described with respect to FIG. 3) electrically coupled with one or more sensors, such as the sensors 211-1 and 211-2. The readout circuitry receives electrical signals from the one or more sensors 211-1 and 211-2 and relays the electrical signals (with or without processing, such as filtering, etc.) to one or more processors of, or operationally connected with, the device 100.

Referring back to FIG. 1, the device 100 includes the piezoelectric actuator 112 located adjacent to a second region 120 (e.g., actuator region, or delivery or ejection region) of the fluid channel 102 downstream from the first region 115. In some embodiments, the piezoelectric actuator 112 deflects (e.g., directs or sorts) the respective particles flowing through the fluid channel 102 to respective output channels 104-1, 104-2, and 104-3 based on signals from the one or more sensors 211-1 and 211-2. In some embodiments, the piezoelectric actuator 112 is located laterally to the second region 120 (e.g., with a contiguous fluid connection to the particle flow path). In some embodiments, the piezoelectric actuator 112 is located below the second region 120. In some embodiments, there are at two of the first piezoelectric actuators 112 in the device 100, each of the at least two of the first piezoelectric actuators 112 being located laterally to the second region 120 on opposite sides of the channel 102. In some embodiments, the at least two of the first piezoelectric actuators 112 are located below the second region 120.

In some embodiments, the piezoelectric actuator 112 includes two or more piezoelectric actuators elements (e.g., each element being a MEMS actuator). In some embodiments, piezoelectric actuator 112 is electrically coupled to the actuation circuitry (e.g., actuation circuitry 310 described with respect to FIG. 3) via electrodes. In some embodiments, when activated using an appropriate electrical signal (e.g., with a specific voltage and pulse width) from the actuation circuitry, the piezoelectric actuator 112 is configured for deflecting or sorting charged particles (which have been manipulated using an electrical field) or non-charged particles, when the particles come into proximity to the piezoelectric actuator 112, toward a specific one of the output channels 104-1, 104-2, and 104-3 or a specific one of output sub-regions 106-1, 106-2 and 106-3 such that the particles can be collected for downstream processing.

In some embodiments, the device 100 includes one or more channel dividers 125 located between the second region 120 and the output channels 104-1, 104-2, and 104-3.

In some embodiments, the expansion region 102-B is between the first region 115 and the second region 120, wherein the first region 115 is characterized by a first cross-section and the expansion region 102-B is characterized by a second cross-section greater than the first cross-section.

Figure 3:
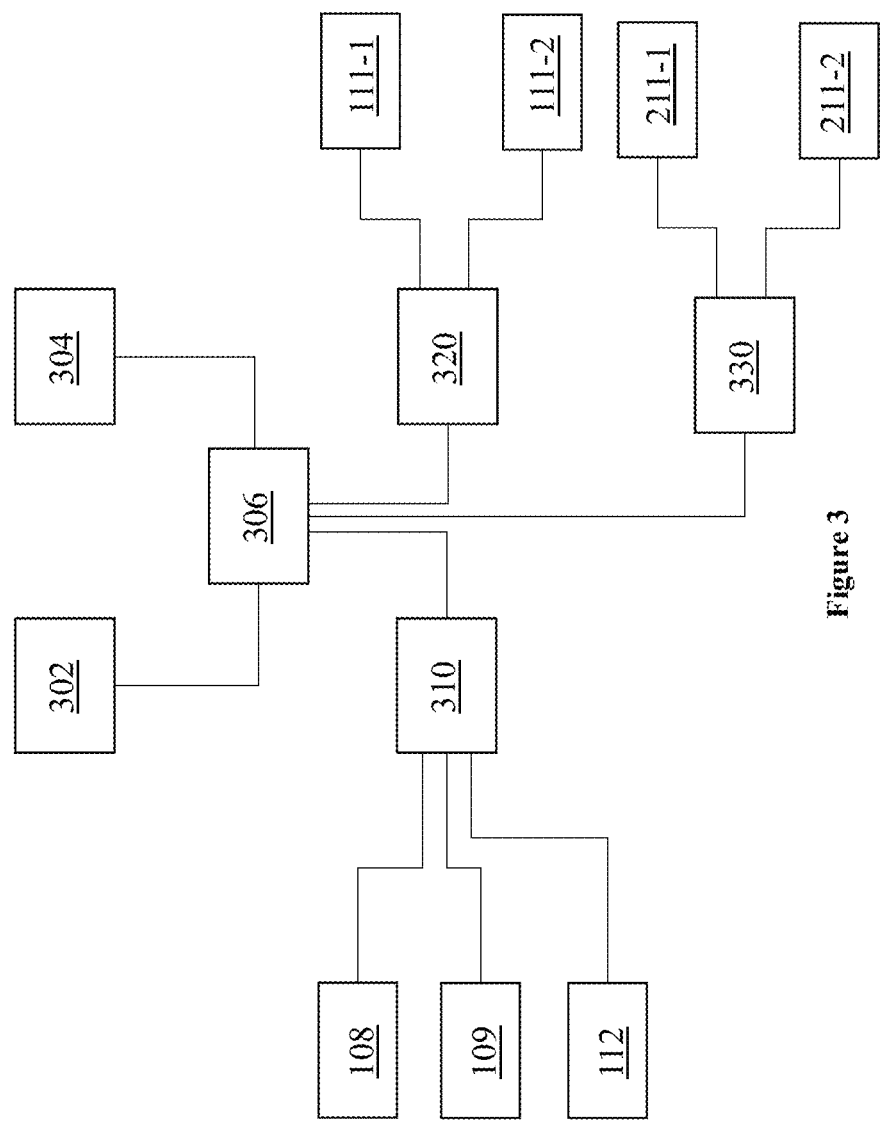
FIG. 3 is a block diagram illustrating electrical components for sensing and sorting cells in accordance with some embodiments.

FIG. 3 is a block diagram illustrating electrical components for sensing and sorting particles in a fluid channel in accordance with some embodiments. In some embodiments, the device (e.g., the device 100) includes one or more processors 302 and memory 304. In some embodiments, the memory 304 includes instructions for execution by the one or more processors 302. In some embodiments, the stored instructions include instructions for receiving the signals from the one or more sensors 211-1 and 211-2, and e.g., after particle signal processing (phenotype creation), providing actuation signals to the piezoelectric actuator 112 (and/or to the piezoelectric actuators 108 and the piezoelectric actuator 109). In some embodiments, the actuation signals for the different piezoelectric actuators may be configured such that each piezoelectric actuator creates oscillations at a different frequency from a frequency of oscillations of another of the piezoelectric actuators. In some embodiments, the stored instructions include instructions for providing actuation signals of a first type in response to receiving sensor signals of a first type and provide actuation signals of a second type distinct from the actuation signals of the first type in response to receiving sensor signals of a second type distinct from the sensor signals of the first type.

In some embodiments, the device also includes an electrical interface 306 coupled with the one or more processors 302 and the memory 304.

In some embodiments, the device further includes actuation circuitry 310, which is coupled to one or more piezoelectric actuators, such as the piezoelectric actuators 108, the piezoelectric actuator 109, and the piezoelectric actuator 112. The actuation circuitry 310 sends electrical signals to the one or more piezoelectric actuators 108, 109, and 112 to initiate actuation of the one or more piezoelectric actuators.

In some embodiments, the device further includes driver circuitry 320, which is coupled to one or more electrodes, such as the electrodes 111-1 and 111-2. The driver circuitry 320 sends electrical signals to the one or more electrodes 111-1 and 111-2 to generate an electrical field using the one or more electrodes for charging at least a subset of particles flowing through the fluid channel 102.

In some embodiments, the device further includes readout circuitry 330, which is coupled to one or more sensors, such as the sensors 211-1 and 211-2. The readout circuitry 330 receives electrical sensor signals indicative of electrical properties (e.g., impedance) of one or more particles (e.g., cells) from the one or more sensors 211-1 and 211-2, and provides the electrical signals (with or without processing) to the one or more processors 302 via the electrical interface 306.

In some embodiments, the stored instructions for execution by the one or more processors 302 include instructions for processing the sensor signals from the readout circuitry 330 and determining one or more impedance values of the one or more cells based on the sensor signals. In some embodiments, determining the one or more impedance values includes determining a magnitude and a phase delay (e.g., for determining real and imaginary components of the impedance value).

In some embodiments, the stored instructions for execution by the one or more processors 302 include instructions for creating phenotype of a cell using on the impedance values. The measured impedance values are frequency dependent and exhibit characteristic frequency response for each of different cellular features of the cell, e.g., the size of the cell, membrane capacitance, cytoplasm conductivity (and other sub-cellular and nuclear properties). As such, using the frequency responses, the one or more processors 302 identify or create phenotype of the cell based on the size of the cell, membrane capacitance, cytoplasm conductivity.

Figure 4:
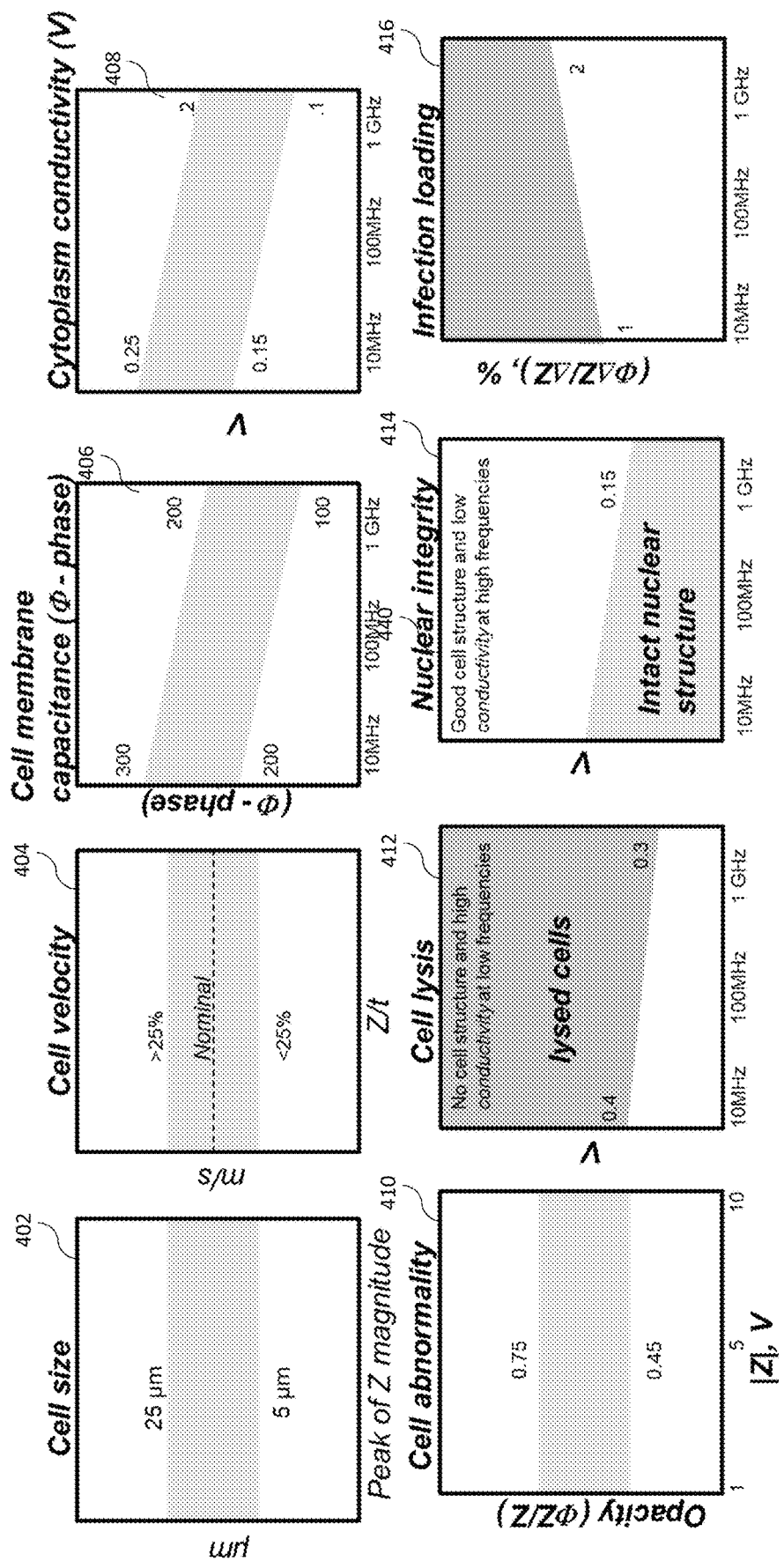
FIG. 4 shows various example thresholds associated with cell characteristics in accordance with some embodiments.

In some embodiments, the stored instructions for execution by the one or more processors 302 include instructions for analyzing the cell phenotype and categorizing or determining a cell type of the cell (among several different cell types) based on the cell phenotype analysis. For example, categorizing or determining the cell types is based on a threshold signature algorithm, in which a threshold value is assigned to each cell type (e.g., a cell is categorized into a particular cell type in accordance with a determination that one or more characteristic values satisfy corresponding threshold values). In some embodiments, the threshold value to categorize or determine a cell type is based on one or more of several cell characteristics (each having varying values as illustrated in FIG. 4, for example). Such cell characteristics may include, but not limited to, cell size (402), cell velocity (404), cell membrane capacitance (406), cytoplasm conductivity (408), cell opacity (410), cell lysis (412), nuclear integrity (414), and cell infection loading (416). In some embodiments, such cell characteristics include other factors.

In some embodiments, the stored instructions for execution by the one or more processors 302 include instructions for determining waveform properties (e.g., voltage, pulse width, etc.) of a specific electrical signal used to actuate or excite the piezoelectric actuator 112 (and/or the piezoelectric actuators 108 and the piezoelectric actuator 109) based on the determined cell type. The specific electrical signal may be determined based on pre-defined user selected criteria, based on which a decision is made to physically sort the cells into different output sub-regions. The specific electrical signal is provided to the actuation circuitry 310 to be provided to the piezoelectric actuator 112. In some embodiments, when activated using the specific electrical signal (e.g., with a specific voltage and pulse width), the piezoelectric actuator 112 generates oscillations that create displacement as well as acoustic waves which causes deflection or sorting of cells of the determined cell type toward a specific one of the output channels 104-1, 104-2, and 104-3 or a specific one of output sub-regions 106-1, 106-2 and 106-3 such that the cells can be collected for downstream processing in the desired output sub-region.

Figure 5:
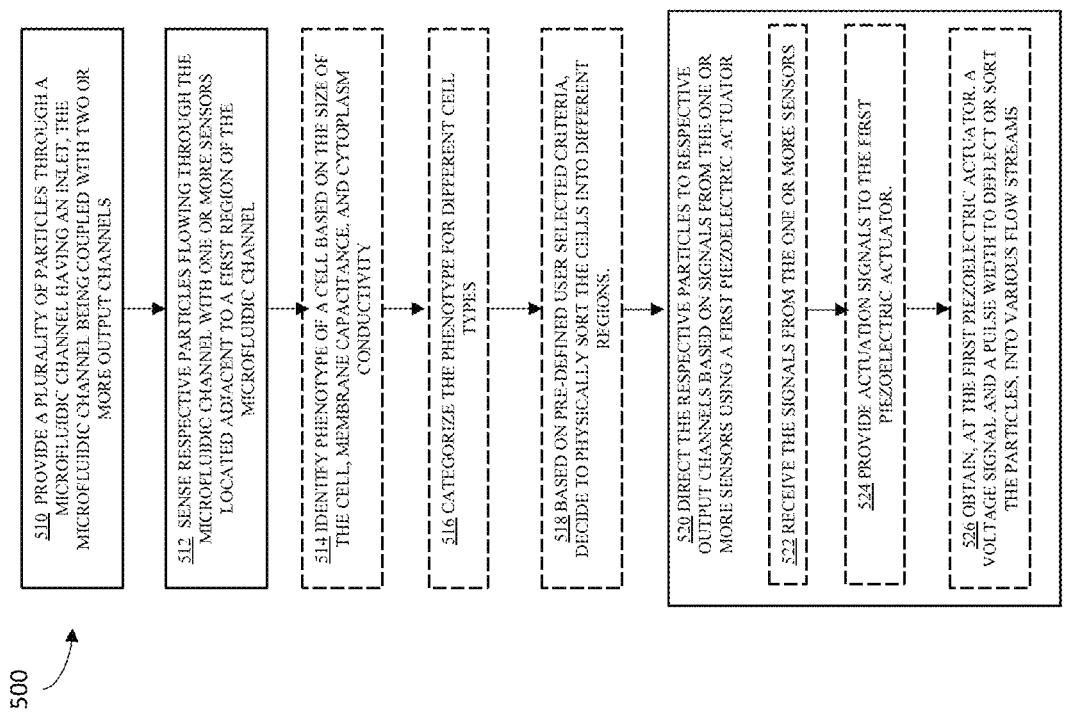
FIG. 5 is a flow diagram illustrating a method of sensing and sorting cells in accordance with some embodiments.

FIG. 5 is a flow diagram illustrating a method 500 of sensing and sorting particles or cells in a fluidic channel in accordance with some embodiments.

The method 500 includes (510) providing a plurality of particles through a microfluidic channel having an inlet, the microfluidic channel being coupled with two or more output channels. For example, a sample fluid with particles (e.g., cells) is provided in the fluid channel 102 with the inlet 103 and the output channels 104-1, 104-2, and 104-3.

In some embodiments, the method 500 includes (512) sensing respective particles flowing through the microfluidic channel with one or more sensors located adjacent to a first region of the microfluidic channel. In some embodiments, the sensing of the respective particles includes sensing the respective particles based on their electrical properties. For example, the particles in the fluid channel 102 are sensed using one or more of the sensors 211-1 and 211-2 in the first region 115.

In some embodiments, the method 500 includes (514) identifying, e.g., by the one or more processors 302, phenotype of a cell based on the size of the cell, membrane capacitance, and cytoplasm conductivity. For example, the one or more processors 302 may access database stored in the memory 304, where the database identifies phenotypes and associated properties (e.g., the size of the cell, membrane capacity, and cytoplasm conductivity). Thus, the one or more processors 302 may identify the phenotype of the cell based on the information included in the database. In some embodiments, the method 500 includes (516) categorizing the phenotype for different cell types, and (518) based on pre-defined user selected criteria, making a decision to physically sort the cells (in the fluid channel 102) into different regions (e.g., output sub-regions 106-1, 106-2, and 106-3).

In some embodiments, the method 500 includes (520) directing the respective particles flown through the microfluidic channel (e.g., the fluid channel 102) to respective output channels of the two or more output channels (e.g., the output channel 104-1, 104-2, and 104-3) based on signals from the one or more sensors (e.g., the sensors 211-1 and 211-2) using a first piezoelectric actuator (e.g., the piezoelectric actuator 112) located adjacent to a second region 120 of the microfluidic channel downstream from the first region 115.

In some embodiments, the method 500 includes (522) receiving the signals from the one or more sensors (e.g., the sensors 211-1 and 211-2), and (524) providing actuation signals to the first piezoelectric actuator (e.g., the piezoelectric actuator 112). In some embodiments, actuation signals of a first type are provided in response to receiving sensor signals of a first type, and actuation signals of a second type distinct from the actuation signals of the first type are provided in response to receiving sensor signals of a second type distinct from the sensor signals of the first type.

In some embodiments, the method 500 includes (526) obtaining, at the first piezoelectric actuator, a voltage signal and a pulse width to deflect or sort the particles, when the particles come into proximity to the first piezoelectric actuator, into various flow streams such that the particles are collected for downstream processing. For example, the piezoelectric actuator 112 obtains a specific electrical signal (e.g., with a specific voltage and pulse width), and based on the specific electrical signal, generates oscillations that create displacement as well as acoustic waves which causes deflection or sorting of cells of the determined cell type toward a specific one of the output channels 104-1, 104-2, and 104-3 or a specific one of output sub-regions 106-1, 106-2 and 106-3. The deflected or sorted cells can be collected for downstream processing in the desired output sub-region.

In some embodiments, the method 500 includes, subsequent to obtaining the voltage signal and the pulse width, dampening oscillations in the first piezoelectric actuator (e.g., oscillations of a piezoelectric membrane in the first piezoelectric actuator). In some operations, dampening the oscillations in the first piezoelectric actuator facilitates maintaining a continuous laminar flow in one or more output channels 104-1, 104-2, or 104-3.

Some embodiments may be described with respect to the following clauses. Clause 1: A microfluidic device, comprising:
a substrate with a microfluidic channel having an inlet, the microfluidic channel being coupled with two or more output channels;
one or more sensors located adjacent to a first region of the microfluidic channel for sensing respective particles flown through the microfluidic channel; and
a first piezoelectric actuator located adjacent to a second region of the microfluidic channel downstream from the first region for deflecting the respective particles flowing through the microfluidic channel to respective output channels of the two or more output channels based on signals from the one or more sensors.

Clause 2: The microfluidic device of clause 1, wherein:
the microfluidic channel includes an expansion region between the first region and the second region, wherein the first region is characterized by a first cross-section and the expansion region is characterized by a second cross-section greater than the first cross-section.

Clause 3: The microfluidic device of clause 1 or 2, wherein:
the first piezoelectric actuator is located laterally to the second region.

Clause 4: The microfluidic device of clause 1 or 2, wherein:
the first piezoelectric actuator is located below the second region.

Clause 5: The microfluidic device of clause 1 or 2, comprising at least two of the first piezoelectric actuators, wherein:
each of the at least two of the first piezoelectric actuators is located laterally to the second region on opposite sides of the microfluidic channel.

Clause 6: The microfluidic device of clause 1 or 2, comprising at least two of the first piezoelectric actuators, wherein the at least two of the first piezoelectric actuators are located below the second region.

Clause 7. The microfluidic device of clause 1 or 2, wherein the first piezoelectric actuator is located laterally to the microfluidic channel.

Clause 8: The microfluidic device of any of clauses 1-7, further comprising:
one or more processors electrically coupled to the one or more sensors for receiving the signals from the one or more sensors and configured for providing actuation signals to the first piezoelectric actuator.

Clause 9: The microfluidic device of clause 8, wherein:
the one or more processors are configured to provide actuation signals of a first type in response to receiving sensor signals of a first type and provide actuation signals of a second type distinct from the actuation signals of the first type in response to receiving sensor signals of a second type distinct from the sensor signals of the first type.

Clause 10: The microfluidic device of any of clauses 1-9, further comprising:
two or more piezoelectric actuators, a respective piezoelectric actuator of the two or more piezoelectric actuators located adjacent to a respective output channel of the two or more output channels for ejecting one or more particles.

Clause 11: The microfluidic device of clause 10, wherein:
the two or more piezoelectric actuators include a layer of piezoelectric material coupled to silicon on insulator.

Clause 12: The microfluidic device of any of clauses 1-11, further comprising:
one or more channel dividers located between the second region and the two or more output channels.

Clause 13: The microfluidic device of any of clauses 1-12, further comprising:
a plurality of pillars for separating particles.

Clause 14: A method, comprising:
providing a plurality of particles through a microfluidic channel having an inlet, the microfluidic channel being coupled with two or more output channels;
sensing respective particles flowing through the microfluidic channel with one or more sensors located adjacent to a first region of the microfluidic channel; and
directing the respective particles flown through the microfluidic channel to respective output channels of the two or more output channels based on signals from the one or more sensors using a first piezoelectric actuator located adjacent to a second region of the microfluidic channel downstream from the first region.

Clause 15: The method of clause 14, wherein:
sensing the respective particles includes sensing the respective particles based on their electrical properties.

Clause 16: The method of clause 14 or 15, further comprising:
calculating the flow velocity of the cell.

Clause 17: The method of any of clauses 14-16, wherein the respective particles include cells, the method further comprising identifying phenotype of a cell based on the size of the cell, membrane capacitance, and cytoplasm conductivity.

Clause 18: The method of clause 17, further comprising categorizing the phenotype for different cell types.

Clause 19: The method of clause 17 or 18, wherein:
based on pre-defined user selected criteria, a decision is made to physically sort these cells into different regions.

Clause 20: The method of any of clauses 14-19, further comprising:
obtaining, at the first piezoelectric actuator, a voltage signal and a pulse width to deflect or sort the particles, when the particles come into proximity to the first piezoelectric actuator, into various flow streams such that the particles are collected for downstream processing.

Clause 21: The method of any of clauses 14-20, further comprising:
receiving the signals from the one or more sensors; and providing actuation signals to the first piezoelectric actuator.

Clause 22: The method of clause 21, further comprising:
providing actuation signals of a first type in response to receiving sensor signals of a first type; and
providing actuation signals of a second type distinct from the actuation signals of the first type in response to receiving sensor signals of a second type distinct from the sensor signals of the first type.

The foregoing description, for purpose of explanation, has been described with reference to specific embodiments. However, the illustrative discussions above are not intended to be exhaustive or to limit the scope of claims to the precise forms disclosed. Many modifications and variations are possible in view of the above teachings. The embodiments were chosen and described in order to best explain the principles of the various described embodiments and their practical applications, to thereby enable others skilled in the art to best utilize the principles and the various described embodiments with various modifications as are suited to the particular use contemplated.

What is claimed is:

1. A microfluidic device, comprising:
a substrate with a microfluidic channel having an inlet, a first region, an expansion region, and a second region, the microfluidic channel being coupled with two or more output channels, wherein:
the first region has a first width;
the second region is downstream from the first region and upstream from the two or more output channels; and
the expansion region is between the first region and the second region, has a second width that is greater than the first width, and is configured to reduce a velocity of respective particles flowing through the microfluidic channel;
one or more sensors located adjacent to the first region of the microfluidic channel for sensing the respective particles;
an inlet piezoelectric actuator located adjacent to the inlet and configured to facilitate input mixing of samples;
a first piezoelectric actuator located adjacent to the second region of the microfluidic channel and configured to deflect the respective particles to respective output channels of the two or more output channels based on signals from the one or more sensors; and
a set of one or more outlet piezoelectric actuators located adjacent to at least one of the two or more output channels and configured to facilitate ejection of the respective particles.

2. The microfluidic device of claim 1, wherein:
the first piezoelectric actuator is located laterally to the second region.

3. The microfluidic device of claim 1, wherein:
the first piezoelectric actuator is located below the second region.

4. The microfluidic device of claim 1, comprising at least two of the first piezoelectric actuators, wherein:
each of the at least two of the first piezoelectric actuators is located laterally to the second region on opposite sides of the microfluidic channel.

5. The microfluidic device of claim 1, comprising at least two of the first piezoelectric actuators, wherein the at least two of the first piezoelectric actuators are located below the second region.

6. The microfluidic device of claim 1, further comprising:
one or more processors electrically coupled to the one or more sensors for receiving signals from the one or more sensors and configured for providing actuation signals to the first piezoelectric actuator.

7. The microfluidic device of claim 6, wherein the one or more processors are configured to:
provide a first type of actuation signals in response to receiving a first type of the signals from the one or more sensors; and
provide a second type of the actuation signals, distinct from the first type of the actuation signals, in response to receiving a second type of the signals from the one or more sensors distinct from the first type of the signals from the one or more sensors.

8. The microfluidic device of claim 1, wherein:
at least one of the input, first, and outlet piezoelectric actuators includes a layer of piezoelectric material coupled to a silicon-on-insulator structure.

9. The microfluidic device of claim 1, further comprising:
one or more channel dividers located between the second region and the two or more output channels.

10. The microfluidic device of claim 1, further comprising:
a plurality of pillars for separating particles.

11. A method, comprising:
providing a plurality of particles through a microfluidic channel having an inlet, a first region, an expansion region, and a second region, the microfluidic channel being coupled with two or more output channels, wherein:
the first region has a first width;
the second region is downstream from the first region and upstream from the two or more output channels; and
the expansion region is between the first region and the second region and has a second width that is greater than the first width;
input mixing the plurality of particles using an inlet piezoelectric actuator;
slowing, using the expansion region, a velocity of respective particles flowing through the microfluidic channel;
sensing the respective particles flowing through the microfluidic channel with one or more sensors located adjacent to the first region of the microfluidic channel;
directing the respective particles to respective output channels of the two or more output channels based on signals from the one or more sensors using a first piezoelectric actuator located adjacent to the second region of the microfluidic channel; and
ejecting at least a portion of the plurality of particles using a set of one or more outlet piezoelectric actuators.

12. The method of claim 11, wherein:
sensing the respective particles includes sensing the respective particles based on their electrical properties.

13. The method of claim 11, further comprising:
calculating a flow velocity of the respective particles.

14. The method of claim 11, wherein the respective particles include cells, and
the method further comprising identifying a phenotype of a cell based on a size of the cell, a membrane capacitance, and a cytoplasm conductivity.

15. The method of claim 14, further comprising categorizing the phenotype for different cell types.

16. The method of claim 11, further comprising:
obtaining, at the first piezoelectric actuator, a voltage signal and a pulse width to deflect or sort the particles, when the particles come into proximity to the first piezoelectric actuator, into various flow streams such that the particles are collected for downstream processing.

17. The method of claim 11, further comprising:
receiving the signals from the one or more sensors; and
providing actuation signals to the first piezoelectric actuator.

18. The method of claim 17, further comprising:
providing a first type of the actuation signals in response to receiving a first type of the signals from the one or more sensors; and
providing a second type of the actuation signals, distinct from the first type of the actuation signals, in response to receiving a second type of the signals from the one or more sensors distinct from the first type of the signals from the one or more sensors.

19. The microfluidic device of claim 1, wherein:
the respective particles are sorted into respective output channels of the two or more output channels in accordance with a categorization of the respective particles using data from the one or more sensors; and
reducing the velocity of the respective particles via the expansion region allows for increased time for the categorization prior to the sorting.

20. The microfluidic device of claim 1, wherein the set of one or more outlet piezoelectric actuators comprises a plurality of outlet piezoelectric actuators, each outlet piezoelectric actuator of the plurality of outlet piezoelectric actuators configured to facilitate ejection from a respective output channel of the two or more output channels.

* * * * *